Figure 1:
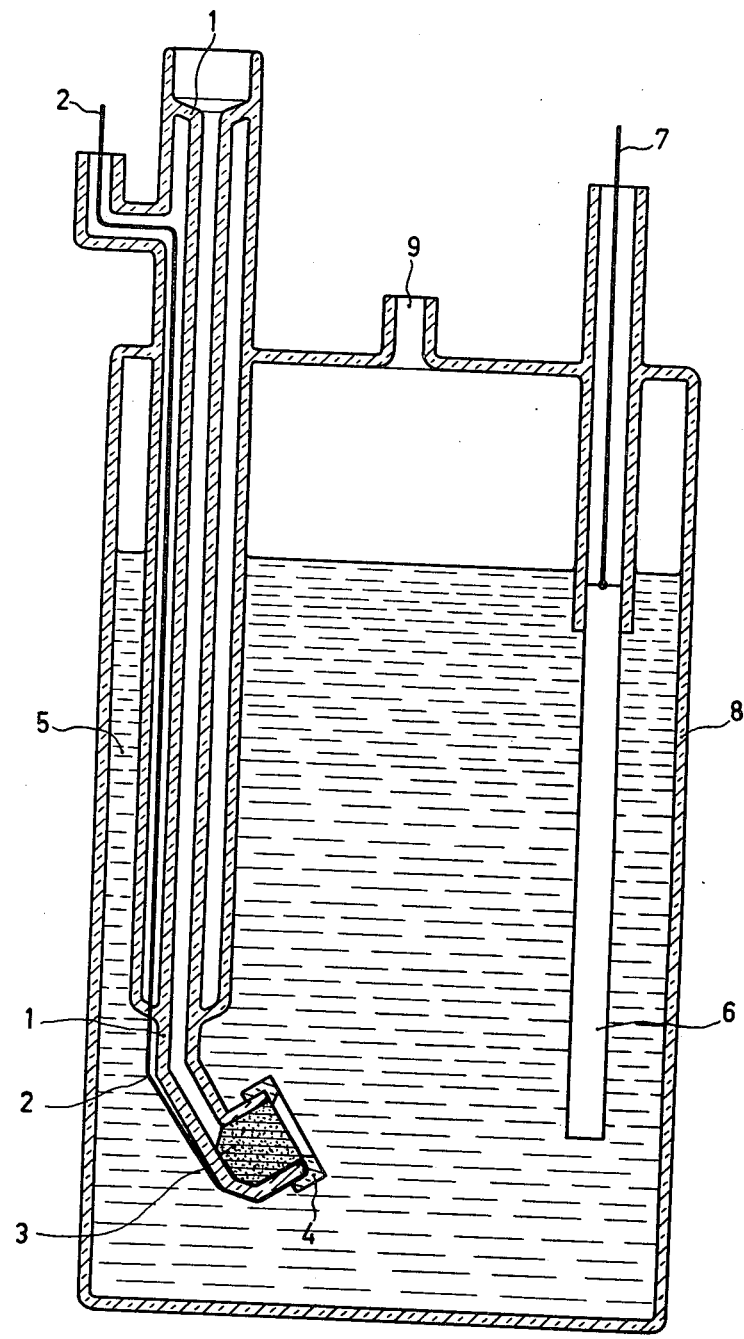

United States Patent [19]

Falkenburg et al.

[11] 3,957,610
[45] May 18, 1976

[54] CELL FOR MEASURING THE AMOUNT OF CO IN A GAS

[75] Inventors: Rudy André Falkenburg; Antonius Wilhelmus Cornelis van Kemenade, both of Eindhoven, Netherlands; Bernhard Lersmacher, Aachen, Germany

[73] Assignee: U.S. Philips Corporation, New York, N.Y.

[22] Filed: Sept. 26, 1974

[21] Appl. No.: 509,481

[30] Foreign Application Priority Data
Oct. 1, 1973   Netherlands...................... 7313451

[52] U.S. Cl............................................. 204/195 R
[51] Int. Cl.²........................................ G01N 27/46
[58] Field of Search ........................ 204/1 T, 195 R

[56] References Cited
UNITED STATES PATENTS
3,450,620   6/1969   Brewer............................ 204/195 R

OTHER PUBLICATIONS

P. Hersch, Beckman Reprint 6213, Beckman Instruments, Inc., pp. 200, 234–236, (1964).

Primary Examiner—G. L. Kaplan
Attorney, Agent, or Firm—Frank R. Trifari; Norman N. Spain

[57] ABSTRACT

The invention relates to a cell for, and a method of, measuring the amount of CO in a gas. After CO has been converted by means of $I_2O_5$ into $CO_2$ and $I_2$, the gas is introduced into an electrolyte solution through an inlet tube which at its orifice is closed by a porous material which acts as a cathode. The iodide produced at the cathode reacts at the anode to form AgI. The cell and the method have important advantages over the known cell and method.

3 Claims, 2 Drawing Figures

CELL FOR MEASURING THE AMOUNT OF CO IN A GAS

The invention relates to a cell for measuring the amount of CO in a gas, which cell is provided with a gas inlet tube near which an electrode is disposed, with an electrolyte solution, with a second electrode and with a gas outlet opening.

Such a cell is described by L. Dubois, A. Zdrojewski and J. L. Monkman, Annual Meeting of the air Pollution Control Association, June 1965, Toronto, Ontario, Canada.

In the known cell the gas mixture to be measured flows through a centrally disposed gas inlet tube into a space which is bounded by a tube made of porous glass which contains an electrode made of platinum gauze. The platinum electrode is wetted by an electrolyte solution with which the outer surface of the lower end of the tube is in contact.

To promote wetting of the platinum electrode and to inhibit the formation of electrolyte crystals due to water evaporation the porous glass tube is wrapped in cheese cloth.

Via the electrolyte solution the cell is electrically connected to a second electrode made of carbon paste.

The known cell has several disadvantages. To achieve optimum wetting of the electrode, to which operation and reproducibility of the cell are related, the cell must be maintained in a horizontal position. Furthermore the gas stream must be in contact with the platinum electrode over a large area to enable complete dissolving of the gas component to be measured in the electrolyte solution on the electrode.

The cell requires a very long time of about 35 minutes, to reach the equilibrium condition.

The cell according to the present invention, which has the object of avoiding the said disadvantages, is characterized in that the gas inlet tube opens below the surface of the electrolyte solution and at the orifice is closed by a porous electrically conductive material which electrochemically is more inert than silver and acts as an electrode, and in that the second electrode is made of silver.

Because the gas stream can only flow into the cell through a porous electrode, intimate contact between the electrode and the gas is ensured. Hence the electrode may be small.

To measure the amount of CO in a gas, the CO is converted by a reaction with $I_2O_5$ in which 1 mole of $I_2$ is produced per 5 moles of CO. This iodine is converted into iodide at the first electrode which the gas stream passes. The mixing effect produced by the rising gas bubbles in the electrolyte solution promotes rapid transport of the iodide to the second electrode. Consequently the rate of the iodide transport is not determined by diffusion, as distinct from the known cell.

At the silver electrode a discrete reaction takes place:

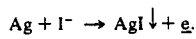

Owing to the above, the cell rapidly reaches equilibrium. As a rule, 90% of the ultimate value is measured within five minutes.

Positioning of the cell is not critical. The cell operates without any change when arranged, for example, at an angle of 45° to the normal.

Examples of a suitable porous electrically conductive material for closing the orifice of the gas inlet tube are foamed carbon, carbon fabrics, foamed carbon or a carbon fabric coated with pyrolytic graphite, sintered silicon carbide, platinum wool or glass frit coated with gold, platinum or pyrolytic carbon. However, a preferred material is graphite felt coated with pyrolytic graphite. This material is mechanically strong and its porosity does not change during use.

The cell may be made of an electrochemically inert material, for example glass or a synthetic material.

The electrolyte solution may have the usual composition and may comprise, for example, a buffered aqueous KBr solution. The solution may contain, for example, 0.1 to 5 moles of KBr/liter, preferably 1 to 3 moles of KBr/l. The buffer may be, for example, $NaH_2PO_4$/$Na_2HPO_4$. The concentration of the buffer is not critical. However, if the concentration is very low, account must be taken of the fact that the pH value of the electrolyte solution may decrease after a comparatively short time, which may affect measurements. The solution preferably contains 0.1 mole/l of either buffer component.

The cell according to the invention may be used in a method of measuring CO in a gas. Hence the invention also relates to a method of measuring the amount of CO in a gas in which by means of CO iodine is liberated from $I_2O_5$ and its amount is electrochemically measured, which method is characterized in that the iodine-containing gas is introduced into an electrolyte solution through an inlet which opens in the electrolyte solution and at its orifice is closed by a porous electrically conductive material which electrochemically is more inert than silver and acts as a cathode, and that the resulting iodide is converted into AgI at a silver anode placed in the electrolyte solution.

When carrying out the method a voltage of 350 mV to 540 mV is set up across the electrodes. As a rule, a voltage between 400 mV and 500 mV is used. The electrode voltage preferably is 480 mV.

Figure 2:
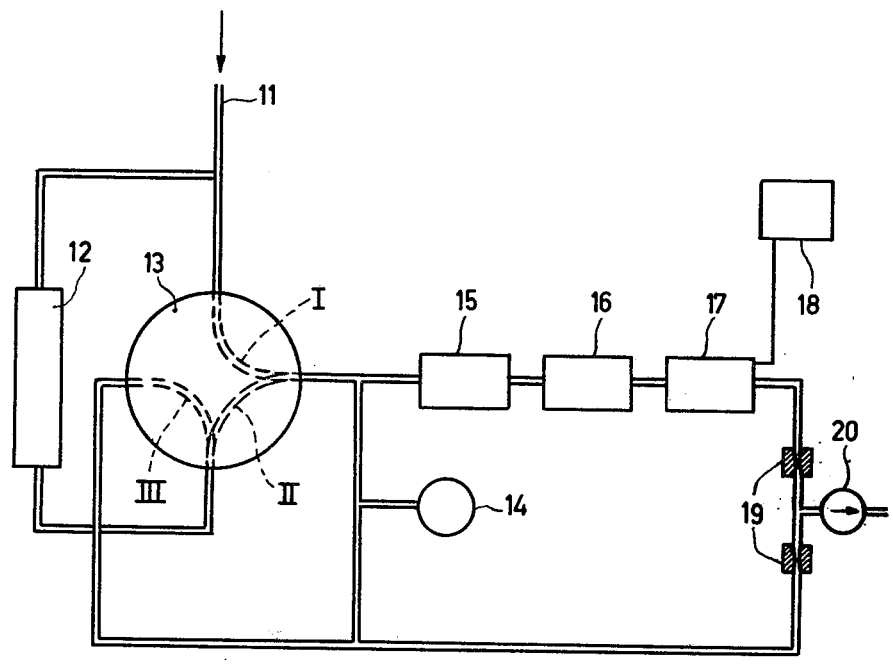

An embodiment of the invention will now be described, by way of example, with reference to the accompanying diagrammatic drawings, in which FIG. 1 is a cross-sectional view of the cell and the electrodes, and FIG. 2 shows schematically a measuring set-up in which the cell can be used.

Referring now to FIG. 1, a gas inlet tube is denoted by 1. A platinum wire 2 is connected to a porous electrically conductive material 3. This material is fixed in the orifice of the tube 1 by means of a nylon ring 4. The electrolyte solution is designated by 5. A silver electrode 6 is connected to the exterior by means of a silver wire 7. A casing 8 of the cell is formed with a gas outlet 9.

In FIG. 2 the gas is introduced at 11. 12 is a null filter filled with activated carbon, manganese oxide and copper oxide (for example activated carbon and hopcalite). 13 is a three-way valve, 14 a source of CO and 15 a selective filter, for example an activated-carbon filter. A reactor filled with $I_2O_5$ is designated 16. Reference numeral 17 denotes the measuring cell according to the invention and reference numeral 18 a micro-ammeter or a recorder connected to it. Two capillaries are designated by 19 and a pump by 20.

In the measuring set-up of FIG. 2 the following experiments are performed by means of the measuring cell of FIG. 1.

The electrolyte solution in the measuring cell contained 3 moles of KBr, 0.1 mole of $NaH_2PO_4$ and 0.1 mole of $Na_2HPO_4$ per liter. The cell was placed in a water bath having a temperature of 37°C.

The reactor 16 was maintained at a temperature of 150°C.

The pump 20 induced 250 ml of gas at 11, 100 ml of which passed through the measuring cell 17.

With a three-way valve in position II air — from which any CO had been removed by the filter 12 — was passed through the measuring cell to determine the zero value. This was $1.4\mu A$.

Then the valve 13 was set to the position III so that air from which CO had been removed in the filter 12 flowed past the source 14 of CO to the measuring cell. The source of CO was a vessel which was fed with CO at a pressure of one atmosphere above atmospheric pressure from a CO gas cylinder and which through a diffusion membrane delivered CO to the air stream in an amount of 5.5 parts per million. This amount was determined by gas chromatography.

4 minutes after the valve 13 had been set to position III a current of $12.6\mu A$ was measured, corrected for the zero value. This is 90% of the ultimate value of $14.0\mu A$ which was measured 15 minutes afterwards.

Then air containing 3 parts per million of CO — measured by gas chromatography — was induced through the inlet opening and the valve 13 was set to the position I, $7.6\mu A$ being measured 4 minutes afterwards.

What is claimed is:

1. A cell for measuring the amount of CO in a gas by electrochemically determining the amount of iodine liberated by the reaction of the CO on $I_2O_5$ in an electrolytic solution, said cell comprising a container for said solution, a gas inlet tube with a gas outlet opening below the surface of said solution for transporting the CO containing gas into said solution, a porous electrically conductive material electrode positioned to plug the outlet opening of said gas inlet tube selected from the group consisting of foamed carbon coated with pyrolytic graphite, carbon fabric coated with pyrolytic graphite and graphite felt coated with pyrolytic graphite and a silver electrode positioned in said solution and away from said gas inlet tube.

2. Cell as claimed in claim 1, characterized in that the porous electrically conductive material is graphite felt coated with pyrolytic graphite.

3. The cell of claim 1 wherein the porous electrically conductive material electrode is selected from the group consisting of foamed carbon and carbon fabric.

* * * * *